(12) United States Patent
Tashiro

(10) Patent No.: US 9,545,287 B2
(45) Date of Patent: Jan. 17, 2017

(54) MEDICAL PORTABLE TERMINAL DEVICE THAT IS CONTROLLED BY GESTURE OR BY AN OPERATION PANEL

(71) Applicant: OLYMPUS CORPORATION, Tokyo (JP)

(72) Inventor: Koichi Tashiro, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/794,381

(22) Filed: Jul. 8, 2015

(65) Prior Publication Data

US 2015/0305813 A1 Oct. 29, 2015

Related U.S. Application Data

(63) Continuation of application No. PCT/JP2014/065184, filed on Jun. 9, 2014.

(30) Foreign Application Priority Data

Jul. 22, 2013 (JP) .................................. 2013-151851

(51) Int. Cl.
*H04N 7/18* (2006.01)
*A61B 19/00* (2006.01)
(Continued)

(52) U.S. Cl.
CPC .............. *A61B 19/00* (2013.01); *A61B 18/14* (2013.01); *A61B 34/25* (2016.02); *A61B 90/08* (2016.02);
(Continued)

(58) Field of Classification Search
USPC .......................................................... 348/74
See application file for complete search history.

(56) References Cited

U.S. PATENT DOCUMENTS 5,594,469 A * 1/1997 Freeman .............. G05B 19/106
345/157
7,702,130 B2 * 4/2010 Im ........................... G06F 3/017
382/103
(Continued)

FOREIGN PATENT DOCUMENTS

EP 1974671 A1 10/2008
EP 2612591 A1 7/2013
(Continued)

OTHER PUBLICATIONS

Aug. 19, 2014 International Search Report issued in International Application No. PCT/JP2014/065184.
(Continued)

*Primary Examiner* — Leron Beck
(74) *Attorney, Agent, or Firm* — Oliff PLC

(57) ABSTRACT

A medical portable terminal device includes an operation panel section including a touch panel for a first operator placed in a non-sterilized area to operate and configured to be capable of controlling operations of a plurality of medical instruments disposed in the non-sterilized area, an image pickup section configured to pick up an image of a region where a second operator performs operation of a gesture, a recognizing section configured to recognize the operation of the gesture from the picked-up image, an operation-list memorizing section configured to memorize an operation list for causing the plurality of medical instruments to perform a plurality of operations associated with a recognition result, and a control section configured to switch between control of the plurality of medical instruments based on operation of the operation panel section and control of the plurality of medical instruments based on the operation of the gesture.

12 Claims, 10 Drawing Sheets

(51) Int. Cl.
    *A61B 18/14*     (2006.01)
    *G06F 3/01*     (2006.01)
    *H04N 5/232*     (2006.01)
    *A61B 17/00*     (2006.01)
    *A61N 7/02*     (2006.01)
    *A61B 18/00*     (2006.01)
    *A61B 18/12*     (2006.01)
    *H04N 5/225*     (2006.01)

(52) U.S. Cl.
    CPC ............ *A61B 90/30* (2016.02); *A61B 90/36* (2016.02); *A61B 90/361* (2016.02); *G06F 3/017* (2013.01); *H04N 5/23203* (2013.01); *H04N 5/23216* (2013.01); *A61B 18/12* (2013.01); *A61B 2017/00199* (2013.01); *A61B 2017/00207* (2013.01); *A61B 2017/00221* (2013.01); *A61B 2017/00225* (2013.01); *A61B 2018/00595* (2013.01); *A61B 2018/00607* (2013.01); *A61B 2018/00982* (2013.01); *A61B 2018/1412* (2013.01); *A61B 2034/2065* (2016.02); *A61B 2034/256* (2016.02); *A61B 2034/258* (2016.02); *A61N 7/02* (2013.01); *H04N 2005/2255* (2013.01)

(56) References Cited

U.S. PATENT DOCUMENTS

| | | | | |
|---|---|---|---|---|
| 9,229,533 | B2* | 1/2016 | Shigeta | G06F 3/048 |
| 2007/0073137 | A1* | 3/2007 | Schoenefeld | A61B 90/36 |
| | | | | 600/407 |
| 2008/0019393 | A1* | 1/2008 | Yamaki | A61B 5/0002 |
| | | | | 370/467 |
| 2008/0242993 | A1* | 10/2008 | Shin | A61B 8/00 |
| | | | | 600/449 |
| 2008/0253519 | A1* | 10/2008 | Bonfiglio | A61B 6/00 |
| | | | | 378/65 |
| 2009/0282371 | A1* | 11/2009 | Curl | G06F 19/327 |
| | | | | 715/863 |
| 2010/0192105 | A1* | 7/2010 | Kim | G06F 3/0488 |
| | | | | 715/834 |
| 2011/0242305 | A1* | 10/2011 | Peterson | G01S 15/003 |
| | | | | 348/77 |
| 2012/0116416 | A1* | 5/2012 | Neff | A61B 19/2203 |
| | | | | 606/130 |
| 2013/0174077 | A1 | 7/2013 | Asami et al. | |
| 2014/0002624 | A1 | 1/2014 | Nemoto et al. | |
| 2014/0049465 | A1* | 2/2014 | Tremaine | G06F 3/017 |
| | | | | 345/156 |

FOREIGN PATENT DOCUMENTS

| | | |
|---|---|---|
| EP | 2679140 A1 | 1/2014 |
| JP | 2003164412 A | 6/2003 |
| JP | 2003223216 A | 8/2003 |
| JP | 2008237913 A | 10/2008 |
| JP | 2010182014 A | 8/2010 |
| JP | 2012048602 A | 3/2012 |
| WO | 2011/060171 A1 | 5/2011 |
| WO | 2011/085813 A1 | 7/2011 |
| WO | 2012129669 A1 | 10/2012 |
| WO | 2013099580 A1 | 7/2013 |

OTHER PUBLICATIONS

Aug. 30, 2016 Extended European Search Report issued in European Patent Application No. 14830346.4.

* cited by examiner

TO SYSTEM CONTROLLER 15

FIG. 5

| OPERATION PATTERN (LIST) | OPERATION CONTENT |
|---|---|
| FIRST OPERATION PATTERN CORRESPONDING TO FIRST GESTURE | OPERATION RECEPTION FOR ELECTRIC KNIFE |
| SECOND OPERATION PATTERN CORRESPONDING TO SECOND GESTURE | OUTPUT CHANGING OPERATION (INCREASE) FOR ELECTRIC KNIFE |
| THIRD OPERATION PATTERN CORRESPONDING TO THIRD GESTURE | OUTPUT CHANGING OPERATION (REDUCTION) FOR ELECTRIC KNIFE |
| FOURTH OPERATION PATTERN CORRESPONDING TO FOURTH GESTURE | OPERATION RELEASE FOR ELECTRIC KNIFE |
| . . . | . . . |

MEDICAL PORTABLE TERMINAL DEVICE THAT IS CONTROLLED BY GESTURE OR BY AN OPERATION PANEL

CROSS REFERENCE TO RELATED APPLICATION

This application is a continuation application of PCT/JP2014/065184 filed on Jun. 9, 2014 and claims benefit of Japanese Application No. 2013-151851 filed in Japan on Jul. 22, 2013, the entire contents of which are incorporated herein by this reference.

BACKGROUND OF THE INVENTION

1. Field of the Invention

The present invention relates to a medical portable terminal device used for operations of medical instruments.

2. Description of the Related Art

A large number of medical instruments are used when a surgical operation is performed. Therefore, there has been proposed a surgical medical system that enables a nurse to easily operate the large number of medical instruments from one place.

As a first conventional example, Japanese Patent Application Laid-Open Publication No. 2012-48602 discloses, for the purpose of making it possible to more easily acquire desired medical information with more intuitive operation, a medical information display device in which a user interface for acquisition condition input receives an input of a gesture during display of a subject external view image (a human body icon), an acquisition-condition specifying section specifies, on the basis of a type of the gesture discriminated by a gesture-type analyzing section or the like and a region corresponding to the type of the gesture, a medical information acquisition condition for acquiring medical information corresponding to the gesture, and a medical-information acquiring section acquires medical information satisfying the specified medical information acquisition condition from a medical information acquisition database and displays the medical information with display means.

As a second conventional example, Japanese Patent Application Laid-Open Publication No. 2010-182014 discloses a device in which a camera that photographs a surgeon in a sterilized area and a gesture recognizing section that recognizes, with the camera, a gesture of the surgeon performing a surgical operation are provided in a medical information terminal. The device provides, according to a gesture of a hand of the surgeon, the surgeon with information such as monitoring information and a test result of a patient.

SUMMARY OF THE INVENTION

A medical portable terminal device according to an aspect of the present invention includes: an operation panel section including a touch panel for a first operator placed in a non-sterilized area to operate and configured to be capable of controlling, according to touch operation on the touch panel, operations of a plurality of medical instruments disposed in the non-sterilized area; an image pickup section configured to pick up an image of a region where a second operator performs operation of a gesture; a recognizing section configured to recognize the operation of the gesture from the picked-up image picked up by the image pickup section; an operation-list memorizing section configured to memorize an operation list for causing the plurality of medical instruments to perform a plurality of operations associated with a recognition result of the recognizing section; and a control section configured to switch between control of the plurality of medical instruments based on operation of the operation panel section and control of the plurality of medical instruments based on the operation of the gesture.

BRIEF DESCRIPTION OF THE DRAWINGS

FIG. 5 is a diagram showing a part of an operation pattern list memorized in advance;

DETAILED DESCRIPTION OF THE PREFERRED EMBODIMENT

Embodiments of the present invention are explained below with reference to the drawings.

(First Embodiment)

Figure 1:
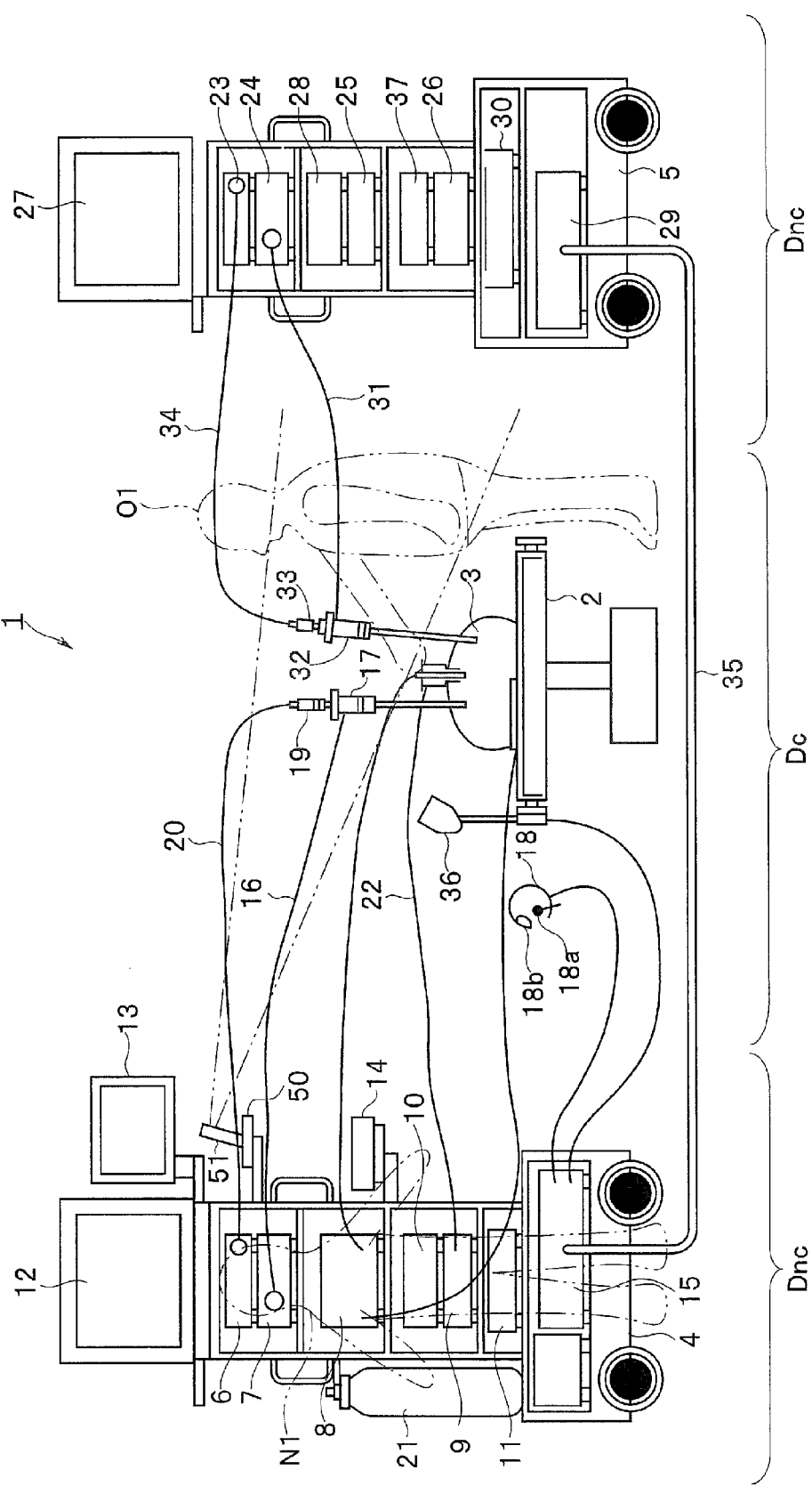
FIG. 1 is a diagram showing an overall configuration of an endoscopic surgery system including a first embodiment of the present invention.

As shown in FIG. 1, in an endoscopic surgery system 1 in the present embodiment, a first trolley 4 and a second trolley 5 functioning as medical instrument mounting tables are disposed on both sides of an operating table 2 on which a patient 3 lies. A plurality of endoscope peripheral instruments functioning as a plurality of medical instruments for performing observation, tests, treatment, recording, and the like are mounted on both the trolleys 4 and 5. Note that a periphery of the operating table 2 on which the patient 3 lies becomes a sterilized area Dc serving as an area set to be clean by sterilization or the like. The first trolley 4 and the second trolley 5 are disposed in non-sterilized areas Dnc on both sides spaced or separated from the sterilized area Dc.

On the first trolley 4, a first TV camera device (or a camera control unit) 6, a first light source device 7, a high-frequency cauterizing device (hereinafter, electric knife device) 8, an insufflation device 9, an ultrasound observation device 10, a printer 11, a first monitor 12, a display panel 13 for a surgeon placed in the sterilized area Dc to perform, for example, check of operation and setting states of instruments, an intensive operation panel 14 functioning as medical instrument operating means including not-shown pointing devices such as a mouse and a touch panel with which a nurse placed in the non-sterilized area Dnc intensively performs operation of the instruments, a system controller 15 functioning as medical instrument intensive control means, and the like are mounted.

The respective instruments mounted on the first trolley 4 are connected to the system controller 15 via a not-shown serial interface cable and are capable of performing bidirectional communication by wire. A microphone set 18 can be connected to the system controller 15. The system controller 15 can recognize, with a voice recognizing section (or a voice recognition circuit) 53 (see FIG. 2), voice inputted from a microphone 18a of the microphone set 18 and control the respective instruments according to voice of the surgeon.

The first light source device 7 is connected to a first endoscope 17 via a light guide cable 16 that transmits illumination light. The first light source device 7 supplies the illumination light of the first light source device 7 to a light guide of the first endoscope 17 and illuminates an affected part or the like in an abdomen of the patient 3 into which an insertion section of the first endoscope 17 is inserted.

A first camera head 19 including an image pickup device is attached to an eyepiece section of the first endoscope 17 to make it possible to pick up, with the image pickup device in the first camera head 19, an optical image of the affected part or the like by an observation optical system of the first endoscope 17, transmit the optical image to the first TV camera device 6 via a camera cable 20, subject the optical image to signal processing with a signal processing circuit in the first TV camera device 6 to generate a video signal, output the video signal to the first monitor 12 via the system controller 15, and display an endoscopic image of the affected part or the like.

An external media recording device such as a not-shown external recording medium (MO) is incorporated in the system controller 15 to make it possible to output an image recorded in the MO or the like to the display panel 13 and display the image.

The system controller 15 is connected to an in-hospital network not-shown, which is provided in a hospital, by a not-shown cable to make it possible to output image data or the like on the in-hospital network to the display panel 13 and display the image data.

A $CO_2$ cylinder 21 is connected to the insufflation device 9 to make it possible to supply a $CO_2$ gas into the abdomen of the patient 3 via an insufflation tube 22 extending from the insufflation device 9 to the patient 3.

A second TV camera device 23, a second light source device 24, an ultrasound treatment device 25, a VTR 26, a second TV monitor 27, a lithotripsy device 28, a pump 37, a shaver 30, a relay unit 29, and the like are mounted on the second trolley 5. The respective devices are connected to the relay unit 29 by not-shown cables and are capable of performing bidirectional communication.

The second light source device 24 is connected to a second endoscope 32 via a light guide cable 31 that transmits illumination light. The second light source device 24 supplies the illumination light of the second light source device 24 to a light guide of the second endoscope 32 and illuminates an affected part or the like in the abdomen of the patient 3 into which an insertion section of the second endoscope 32 is inserted.

A second camera head 33 including an image pickup device is attached to an eyepiece section of the second endoscope 32 to make it possible to pick up, with the image pickup device in the second camera head 33, an optical image of the affected part or the like by an observation optical system of the second endoscope 32, transmit the optical image to the second TV camera device 23 via a camera cable 34, subject the optical image to signal processing with a signal processing circuit in the second TV camera device 23 to generate a video signal, output the video signal to the second monitor 27, and display an endoscopic image of the affected part or the like.

The system controller 15 and the relay unit 29 are connected by a system cable 35.

Further, a remote controller for the surgeon (hereinafter referred to as a remote controller) 36, with which the surgeon performs operation of the devices from the sterilized area Dc, is connected to the system controller 15 via a cable.

An arm is protrudingly provided in a horizontal direction in the first trolley 4. A holder 50 is attached near an end portion of the arm. A medical portable terminal device (hereinafter abbreviated as terminal device) 51 in the first embodiment can be detachably attached to the holder 50.

The terminal device 51 has, for example, a size of approximately 7 inches, which enables the terminal device 51 to be gripped by one hand, and a weight of approximately several hundred grams such that the nurse can easily carry the terminal device 51 and perform various kinds of operation. Note that the terminal device 51 is not limited to the size of approximately 7 inches. The nurse who actually uses the terminal device 51 may be able to select a terminal device out of, for example, terminal devices having one of the sizes of 7 to 11 inches.

In the present embodiment, a nurse N1 in the non-sterilized area Dnc can carry the terminal device 51 and perform operation of various medical instruments shown in FIG. 1 via the system controller 15, for example, when performing touch operation on the intensive operation panel 14. Note that, usually, the intensive operation panel 14 has a size larger than that of the terminal device 51. Therefore, the terminal device 51 is more suitable for carrying.

When the nurse N1 attaches the terminal device 51 to the holder 50, the terminal device 51 is held in a predetermined posture by the holder 50 and set in a state in which there is no motion, in other words, acceleration does not temporally change. The holder 50 forms a holding device that holds the terminal device 51 in the predetermined posture.

In this state, a position of the holder 50 is set to make it possible to pick up an image of a region where a surgeon O1 placed in the sterilized area Dc performs operation of a gesture. Operations of the medical instruments can be controlled on the basis of the operation of the gesture.

In the present embodiment, detecting means for detecting whether the terminal device 51 is in a predetermined operation state is provided to make it possible to automatically switch between an operation function and a control function by the terminal device 51 according to a detection result of the detecting means.

Figure 2:
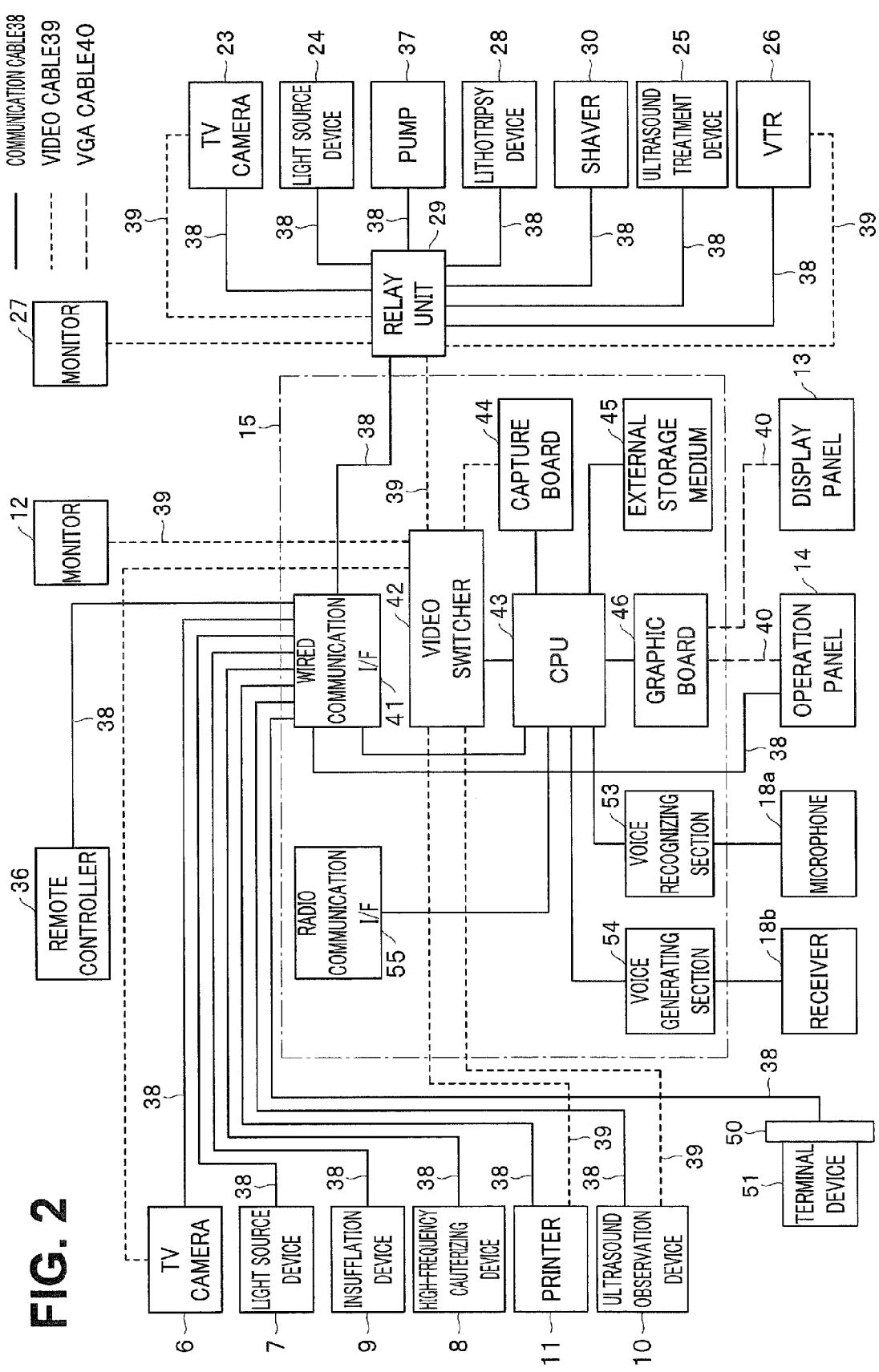
FIG. 2 is a diagram showing a schematic configuration of an electric system of the endoscopic surgery system.

As shown in FIG. 2, the intensive operation panel 14, the remote controller 36, the first TV camera device 6, the first light source device 7, the electric knife device 8, the insufflation device 9, the printer 11, and the ultrasound observation device 10 are respectively connected to a wired communication I/F 41 of the system controller 15 by communication cables 38 to perform transmission and reception of data.

The first monitor 12, the first TV camera device 6, the printer 11, and the ultrasound observation device 10 are connected to a video switcher 42 of the system controller 15 by video cables 39 to be capable of transmitting and receiving video signals. The intensive operation panel 14 and the display panel 13 can receive inputs of VGA images from a graphic board 46 of the system controller 15 via VGA cables 40 and display multi-monitor images.

The second TV camera device 23, the second light source device 24, the ultrasound treatment device 25, the VTR 26, the lithotripsy device 28, the shaver 30, and the pump 37 are connected to the relay unit 29 by the communication cables 38 to perform transmission and reception of data. The second monitor 27, the second TV camera device 23, and the VTR 26 are connected to the relay unit 29 by the video cables 39 to be capable of transmitting and receiving video signals.

The relay unit 29 is connected to the system controller 15 by the cable 35 (see FIG. 1), connected to the wired communication I/F 41 of the system controller 15 via the communication cable 38 in the cable 35, and connected to the video switcher 42 of the system controller 15 via the video cable 39 in the cable 35.

The holder 50 is connected to the wired communication I/F 41 of the system controller 15 via the communication cable 38. When the terminal device 51 is attached (connected) to the holder 50, the terminal device 51 is capable of performing communication by wire with the system controller 15.

The system controller 15 includes, besides the wired communication I/F 41, the video switcher 42, and the graphic board 46, a capture board 44 that captures image data via the video switcher 42. These respective circuits are controlled by a central processing unit (abbreviated as CPU) 43 (having a function of setting-screen generating means).

An external storage medium 45 is connectable to the system controller 15. Image data can be recorded in the external recording medium from the CPU 43 and can be reproduced.

The system controller 15 includes, besides the voice recognizing section 53 that performs recognition of voice, a voice generating section 54 that generates a voice signal for transmitting content corresponding to a recognition result to the surgeon by voice. The voice signal generated by the voice generating section 54 is outputted to a receiver 18*b* of the microphone set 18.

In the present embodiment, the system controller 15 includes, besides the wired communication I/F 41 that forms wired communicating means (or communicating section), a radio communication I/F 55 that performs radio communication with a radio communication I/F 76 (see FIG. 4) that forms radio communicating means (or communicating section) provided in the terminal device 51.

Figure 3A:
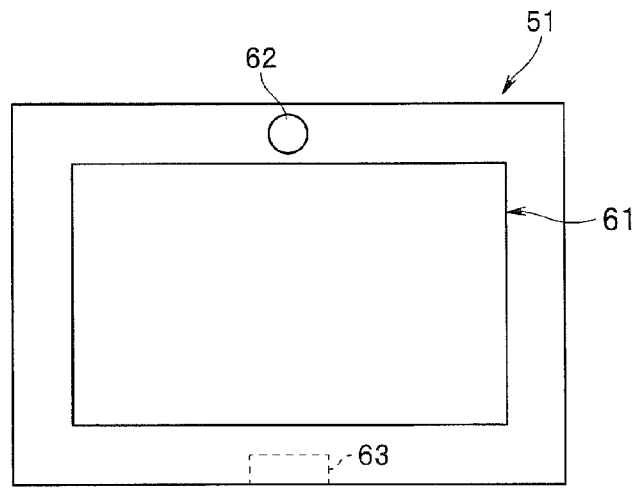
FIG. 3A is a front view showing an external view of a medical portable terminal device in the first embodiment.
Figure 3B:
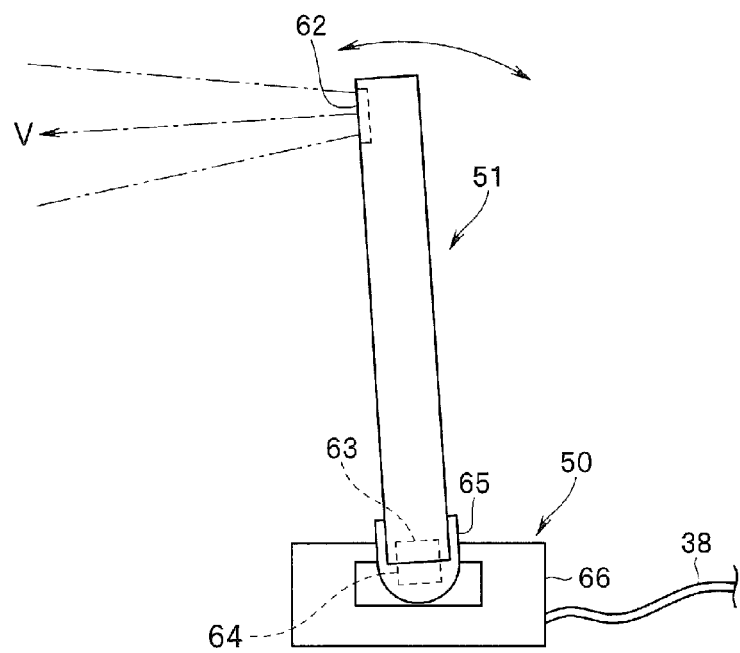
FIG. 3B is a side view showing a state in which the medical portable terminal device is held by a holder.

FIG. 3A shows an external view of the terminal device 51. FIG. 3B shows the terminal device 51 attached to the holder 50 functioning as a holding device.

The terminal device 51 has, for example, a shape of a rectangular plate small in thickness. An operation panel section (or an operation display section) 61 slightly smaller in size than an entire surface and a camera 62 functioning as an image pickup section disposed in a position near an upper part in a center are provided on one plate surface, which is a front surface.

A connector 63 is provided at a lower end, which is an end portion on an opposite side, of the camera 62. The connector 63 is detachably connected to a connector receiver 64 on the holder 50 side.

The holder 50 includes a movable body 65 that holds a lower end of the terminal device 51 and a holding body 66 that holds the turnable movable body 65 at a desired angle. Note that the movable body 65 is held with parts of an outer circumferential surface on both sides of an axis, which is a rotation center of a semi-cylindrical portion of the movable body 65, in contact with a holding section of the holding body 66.

The lower end of the terminal device 51 fits in a recess provided in the movable body 65. When the lower end of the terminal device 51 is fit in the recess, the connector 63 is connected to the connector receiver 64. The movable body 65 is tiltably held by the holding body 66. Note that, in FIG. 3B, the movable body 65 can be fixed in any movable position by a frictional force of a contact surface of the holding section with which the movable body 65 and the holding body 66 are in contact. However, the movable body 65 may be fixed by a screw or the like. The terminal device 51 attached to the movable body 65 is capable of adjusting a tilt angle of plate surfaces of the terminal device 51 in conjunction with the movable body 65 as shown in FIG. 3B. In other words, it is possible to change or adjust a visual field direction V of the camera 62 of the terminal device 51 by adjusting the tilt angle of the plate surfaces of the terminal device 51.

By changing or adjusting the visual field direction V of the camera 62, for example, when the terminal device 51 is attached to the holder 50 as shown in FIG. 1, a visual field of the camera 62 can be set to cover a gesture range of the surgeon (who performs operation of a gesture). Therefore, the holder 50 has a function of a visual-field-range changing section (or a visual-field-range changing device) that mechanically changes a visual field range of the camera 62 functioning as the image pickup section of the terminal device 51. Note that, in a configuration of FIG. 3B, an example including a tilt function for swinging the visual field direction of the camera 62 up and down (direction) is shown. However, a pan function for swinging the visual field direction left and right (direction) may be further provided.

Figure 4:
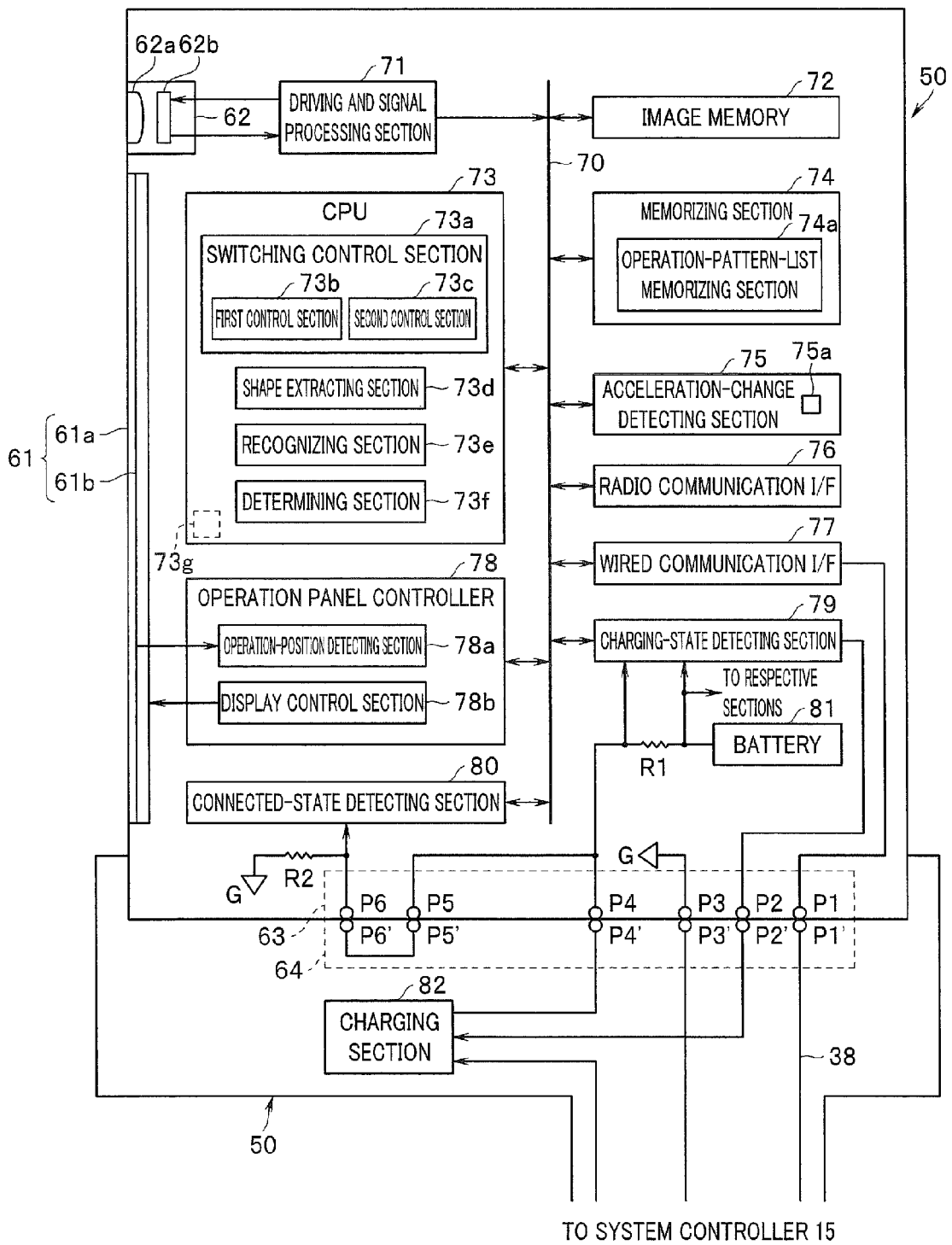
FIG. 4 is a block diagram showing a configuration of an electric system of the medical portable terminal device and the holder.

FIG. 4 shows an internal configuration of the terminal device 51 and the holder 50. As shown in FIG. 4, the camera 62 configuring the image pickup section includes an objective lens 62*a* and an image pickup device 62*b* such as a charge coupled device disposed in an image-forming position of the objective lens 62*a*. The image pickup device 62*b* is connected to a driving and signal processing section (or a driving and signal processing circuit) 71. (A driving section or a driving circuit of) the driving and signal processing section 71 applies a driving signal to the image pickup device 62*b* and causes the image pickup device 62*b* to output a signal of a picked-up image. (A signal processing section or a signal processing circuit of) the driving and signal processing section 71 performs signal processing for the outputted signal. Note that the objective lens 62*a* or the image pickup device 62*b* may be set movable in an optical axis direction to make it possible to variably adjust the visual field range. Alternatively, the driving and signal processing section 71 may electrically change the visual field range.

The driving and signal processing section 71 A/D-converts a video signal (an image signal) subjected to the signal processing and stores the video signal (the image signal) in an image memory 72 connected to a data bus 70 as video data (image data).

A CPU 73 having a function of a control section (or a control circuit) that performs processing such as recognition of a pattern by a gesture from the video data (the image data) and control based on a recognition result, a memorizing section 74 configured by a memory or the like that memorizes in advance a list of operation patterns for operation of a plurality of medical instruments as an operation pattern list (also referred to as an operation list), an acceleration-change detecting section (or an acceleration-change detection circuit) 75 that includes an acceleration sensor 75a and detects a temporal change in acceleration, a radio communication I/F 76, a wired communication I/F 77, an operation panel controller 78, a charging-state detecting section (or a charging-state detection circuit) 79, and a connected-state detecting section (or a connected-state detection circuit) 80 are connected to the data bus 70.

In the terminal device 51, a battery 81 configured by a secondary battery including a rechargeable lithium battery that supplies direct-current power necessary for operations to the driving and signal processing section 71, the image memory 72, . . . , and the connected-state detecting section 80 is also housed.

The operation panel section 61 shown in FIG. 3A includes a display panel 61a that displays an operation guide image representing content and the like of touch operation when the touch operation is performed and a touch panel 61b including a plurality of touch sensors that detect which position in the guide image displayed by the display panel 61a is touch-operated.

The display panel 61a is connected to a display control section (or a display control circuit) 78b in the operation panel controller 78. The display control section 78b controls the operation guide image displayed by the display panel 61a. Note that data of the operation guide image displayed by the display control section 78b is stored (memorized) in, for example, the memorizing section 74 in advance. Therefore, the memorizing section 74 has a function of an operation-guide-image-data storing section (or an operation-guide-image-data storing device) that stores the operation guide image data.

The touch panel 61b is connected to an operation-position detecting section (or an operation-position detection circuit) 78a in the operation panel controller 78. The operation-position detecting section 78a detects, as an operation position (a touch position), a position touched by the nurse N1. The operation-position detecting section 78a determines, from the operation guide image by the display control section 78b, operation content (control content) of a medical instrument corresponding to the operation position touched by the nurse N1 and sends the operation content (the control content) to the CPU 73.

Note that, instead of the operation-position detecting section 78a having the functions explained above, the operation-position detecting section 78a may generate a signal of the touched position and send the signal to the CPU 73 and a first control section (or a first control circuit) 73b of the CPU 73 may determine, from the sent signal, whether the signal is an operation signal of operation for causing the medical instrument to operate.

The CPU 73 has a function of the first control section 73b that performs control to perform an operation of a medical instrument instructed by touch operation of the operation panel section 61 by the nurse N1 (or cause the medical instrument to perform the operation).

The CPU 73 includes, for example, a switching control section (or a switching control circuit) 73a including a control function of the first control section 73b and a control function of a second control section (or a second control circuit) 73c based on operation of a gesture explained below.

In the present embodiment, instead of performing the control function of the first control section 73b and the control function of the second control section 73c in parallel, the switching control section 73a alternatively has the control function of the first control section 73b and the control function of the second control section 73c on the basis of a detection result of a predetermined operation state for the terminal device 51 to improve convenience. In other words, the switching control section (or the switching control circuit) 73a automatically switches between the control function of the first control section 73b and the control function of the second control section 73c on the basis of the detection result of the predetermined operation state for the terminal device 51.

In this case, in a state in which the terminal device 51 is carried by the nurse N1 and the terminal device 51 is moved (a state in which acceleration temporally changes), (the switching control section 73a of) the CPU 73 is set to have the function of the first control section 73b as explained above. In a state in which the terminal device 51 is not moving, more specifically, a state in which the terminal device 51 is attached to the holder 50, (the switching control section 73a of) the CPU 73 is set to have the function of the second control section 73c as explained below. Note that the acceleration-change detecting section 75 has a function of a detecting section (or a detection circuit) that detects the predetermined operation state.

The image data stored in the image memory 72 is captured by the CPU 73. The CPU 73 has a function of a shape extracting section (or a shape extracting circuit) 73d that extracts image data of a shape related to a gesture from the image data. The CPU 73 has a function of a recognizing section 73e that recognizes a pattern related to operation of a gesture from image data of shapes of a plurality of frames extracted by the shape extracting section 73d (or a generating section that generates a pattern related to the operation of the gesture).

The CPU 73 has a function of a determining section (or a determination circuit) 73f that collates (compares) a pattern recognized by a recognizing section (or a recognition circuit) 73e and the operation pattern list memorized (registered) in advance in the memorizing section 74 and determines whether the pattern is a pattern matching the operation pattern list within an allowable error. Therefore, the memorizing section 74 includes an operation-pattern-list memorizing section (or an operation-pattern-list memorizing device) 74a that memorizes a list of a plurality of operation patterns set in advance in order to cause a plurality of medical instruments to respectively perform predetermined operations.

FIG. 5 shows a part of the operation pattern list. In an example shown in FIG. 5, operation content of operation reception (operation receipt) for an electric knife is memorized (registered) with respect to, for example, a first operation pattern corresponding to (operation of) a first gesture. In this case, when the surgeon performs the first gesture equivalent to the first operation pattern, in operation content or control content, operation (of a gesture) for the electric knife is in a received state. When the surgeon performs second and third gestures equivalent to second and third operation patterns, output setting variable operation of the electric knife is performed. When the surgeon performs the second gesture, the output setting is increased. When the surgeon performs the third gesture, the output setting is reduced.

When a fourth gesture is performed, the operation reception for the electric knife is released. Besides, switching of an output mode may be able to be performed by operation of a gesture. Note that the electric knife is connected to the electric knife device 8 via a high-frequency cable. A high-frequency current is supplied to the electric knife from the electric knife device 8 by the high-frequency cable.

For example, in an ultrasound dissection and coagulation treatment instrument functioning as another medical instrument different from the electric knife functioning as the treatment instrument by the high-frequency current also, operation patterns and operation content are memorized (registered) as in the case of the electric knife. The ultrasound dissection and coagulation treatment instrument is connected to the ultrasound treatment device 25 shown in FIG. 1 via an ultrasound cable.

Further, for a medical instrument that does not actively perform treatment for the patient 3, for example, the first monitor 12, switching of an observation mode and the like may be able to be controlled by operation of a gesture.

As shown in FIG. 4, when the determining section 73f determines that the pattern is the matching pattern (i.e., a specific operation pattern), the CPU 73 has the function of the second control section 73c that performs control to perform an operation of a medical instrument corresponding to the pattern (or cause the medical instrument to perform the operation).

The switching control section 73a automatically switches between the functions of the first control section 73b and the second control section 73c on the basis of, for example, a detection result based on the acceleration-change detecting section 75 to reduce a burden of operation of switching by the nurse N1.

By temporally monitoring a sensed signal outputted from the acceleration sensor 75a, which senses acceleration acting on the terminal device 51, and detecting whether the acceleration temporally changes, the acceleration-change detecting section 75 determines whether the terminal device 51 is operating in a state in which the terminal device 51 is carried by the nurse N1. More specifically, the acceleration-change detecting section 75 detects, as detection concerning whether the terminal device 51 is moving, according to whether the terminal device 51 is in the predetermined operation state, whether an absolute value of a temporal change amount of a sensed signal outputted when the acceleration sensor 75a senses acceleration (in other words, a temporal change amount of the acceleration) changes by a threshold, which is set according to the absolute value, or more. The acceleration-change detecting section 75 outputs a determination signal of the determination concerning whether the absolute value is equal to or larger than the threshold to the switching control section 73a of the CPU 73 as a determination signal concerning whether the terminal device 51 is moving.

In a case of a determination result that the terminal device 51 is moving, the switching control section 73a performs control with the function of the first control section 73b. In a case of a determination result that the terminal device 51 is not moving, the switching control section 73a performs control with the function of the second control section 73c. Operations in this case are explained below with reference to FIG. 6A.

In the present embodiment, in association with the determination result concerning whether the terminal device 51 is moving, the connected-state detecting section 80 detects whether the terminal device 51 is connected (attached) to the holder 50. The switching control section 73a performs switching between radio communication and wired communication, control of charging operation, and the like according to a detection result. Therefore, the switching control section 73a has a function of an operation switching section (or an operation-switching control section) that performs switching between an operation of a radio communication of the radio communication I/F 76 functioning as a radio communication section and an operation of the wired communication I/F 77 functioning as a wired communication section.

Note that, when the detecting section detects whether the terminal device 51 is in the predetermined operation state, the detecting section is not limited to detecting, as the predetermined operation state, whether the terminal device 51 is moving. The acceleration-change detecting section 75 may detect whether the absolute value is equal to or larger than the threshold.

In the state in which the terminal device 51 is carried by the nurse N1, the switching control section 73a of the terminal device 51 performs the radio communication with the system controller 15 to control an operation of a medical instrument. In the state in which the terminal device 51 is connected to the holder 50, the switching control section 73a switches between the radio communication to the wired communication to control the operation of the medical instrument.

By performing such switching, it is possible to secure operability (by adoption of the radio communication) in the case in which the terminal device 51 is carried by the nurse N1 and, in the state in which the terminal device 51 is connected to the holder 50, (by adopting the wired communication), control the operation of the medical instrument in a state in which the medical instrument is less affected by a radio wave state of the radio communication.

When the terminal device 51 is connected (attached) to the holder 50 as explained above, the connector 63 of the terminal device 51 is connected to the connector receiver 64 of the holder 50. In this case, a charging section 82 provided in the holder 50 is electrically connected to the battery 81. For example, direct-current power is supplied to the charging section 82 by (a power supply cable in) the communication cable 38 connected to the system controller 15. The charging section 82 converts the direct-current power into a direct-current voltage for charging the battery 81 with a charging circuit on an inside of the charging section 82.

As shown in FIG. 4, an output end of the charging section 82 is connected to a positive electrode of the battery 81 via an electric contact P4' of the connector receiver 64, an electric contact P4 of the connector 63, and a resistor R1. Note that a negative electrode of the battery 81 is connected to a ground G (not shown in the figure). The ground G is connected to an electric contact P3. The electric contact P3 is connected to an electric contact P3' connected to a ground cable.

In the case of a charging state, a charging current flows from the charging section 82 to the batter 81 via the resistor R1. In this case, the charging-state detecting section (or the charging-state detection circuit) 79 monitors a voltage across the resistor R1 and monitors, according to whether the voltage is a threshold or less, whether the battery 81 is in a charging completed state.

When determining that the battery 81 is not in the charging completed state, the charging-state detecting section 79 performs operations for feeding a charging current to the battery 81 and charging the battery 81. When determining that the battery 81 is in the charging completed state, the charging-state detecting section 79 sends a signal for a charging stop to the charging section 82 via electric contacts P2 and P2' to turn off the operation for charging the battery 81, turns off the charging current, and prevents overcharging of the battery 81.

The connected-state detecting section 80 detects, for example, whether electric contacts P5 and P6 respectively connected to electric contacts P5' and P6' for connection sensing are in an unconnected state in which a voltage at the electric contact P6 is approximately a voltage of the ground G or a connected state in which the voltage at the electric contact P6 is a voltage higher than the voltage of the ground G. The electric contact P5 is connected to the electric contact P4, the electric contact P5' and the electric contact P6' conduct electricity, and the electric contact P6 is set to the voltage of the ground G via a resistor R2 for pull-down.

The connected-state detecting section 80 compares the voltage at the electric contact P6 with a threshold voltage slightly higher than the voltage of the ground G. When the voltage at the electric contact P6 is lower than the threshold voltage, the connected-state detecting section 80 determines (detects) that the electric contacts P5 and P6 are in the unconnected state. When the voltage at the electric contact P6 exceeds the threshold voltage, the connected-state detecting section 80 determines (detects) that the electric contacts P5 and P6 are in the connected state.

When a determination (detection) result switches from the unconnected state to the connected state, the connected-state detecting section 80 stops an operation of the radio communication I/F 76 of the terminal device 51 and switches the wired communication I/F 77 to an operating state.

The wired communication I/F 77 is connected to the wired communication I/F 41 of the system controller 15 via electric contacts P1 and P1' and the communication cable 38.

Note that the functions of the switching control section 73a, the first control section 73b, the second control section 73c, the shape extracting section 73d, the recognizing section 73e, and the determining section 73f in the CPU 73 shown in FIG. 4 may be respectively configured using hardware such as dedicated electronic circuits. The switching control section 73a, the first control section 73b, the second control section 73c, the shape extracting section 73d, the recognizing section 73e, and the determining section 73f may be formed using an FPGA (field programmable gate array). For example, the recognizing section 73e may be configured to also perform the function of the shape extracting section 73d. The recognizing section 73e may be configured to also perform the function of the determining section 73f. The recognizing section 73e may be configured to also perform the functions of the shape extracting section 73d and the determining section 73f. One of the charging-state detecting section 79 and the connected-state detecting section 80 in FIG. 4 may perform the functions of both of the charging-state detecting section 79 and the connected-state detecting section 80. The charging-state detecting section 79 and the connected-state detecting section 80 may be configured using CPUs or may be configured using dedicated hardware. The terminal device 51 is not limited to the configuration example shown in FIG. 4. One function may also perform the other functions.

The terminal device 51 in the first embodiment having such a configuration includes the touch panel 61b for the nurse N1 acting as a first operator placed in the non-sterilized area Dnc to operate. The terminal device 51 includes the operation panel section 61 configured to be capable of controlling, according to touch operation on the touch panel 61b, operations of a plurality of medical instruments disposed in the non-sterilized area Dnc, the camera 62 functioning as the image pickup section configured to pick up an image of a region where the surgeon O1 acting as a second operator present in the sterilized area Dc separated from the non-sterilized area Dnc, where the plurality of medical instruments are disposed, performs operation of a gesture, the recognizing section 73e configured to recognize the operation of the gesture from the picked-up image picked up by the image pickup section, the operation-pattern-list memorizing section 74a that forms the operation-list memorizing section configured to memorize an operation list (corresponding to a plurality of predetermined operation patterns by the operation of the gesture) for causing the plurality of medical instruments to perform a plurality of operations associated with a recognition result of the recognizing section 73e, and the switching control section 73a functioning as the control section configured to switch between control of the plurality of medical instruments based on operation of the operation panel section 61 and control of the plurality of medical instruments based on the operation of the gesture.

Action in the present embodiment is now explained with reference to FIGS. 6A and 6B. As a specific example of a case in which the action in the present embodiment is explained, for example, action in a following case is explained.

The nurse N1 carrying the terminal device 51 touch-operates the operation panel section 61 of the terminal device 51 to perform control and setting of operations of various medical instruments, for example, in the non-sterilized area Dnc including a position near the first trolley 4 indicated by an alternate long and two short dashes line in FIG. 1. Before a start of a surgical operation, the nurse N1 moves around to install the various medical instruments and, for example, touch-operate the operation panel section 61 to set an installed plurality of medical instruments in predetermined setting states necessary for performing the surgical operation. However, for example, in a state after the surgical operation is started, a frequency of necessity that the nurse N1 moves and operates the medical instruments decreases. In such a case, the nurse N1 sets (attaches) the carried terminal device 51 in (to) the holder 50. The nurse N1 directly operates the medical instruments or performs operation for controlling operations of the medical instruments from the intensive operation panel 14.

Figure 7:
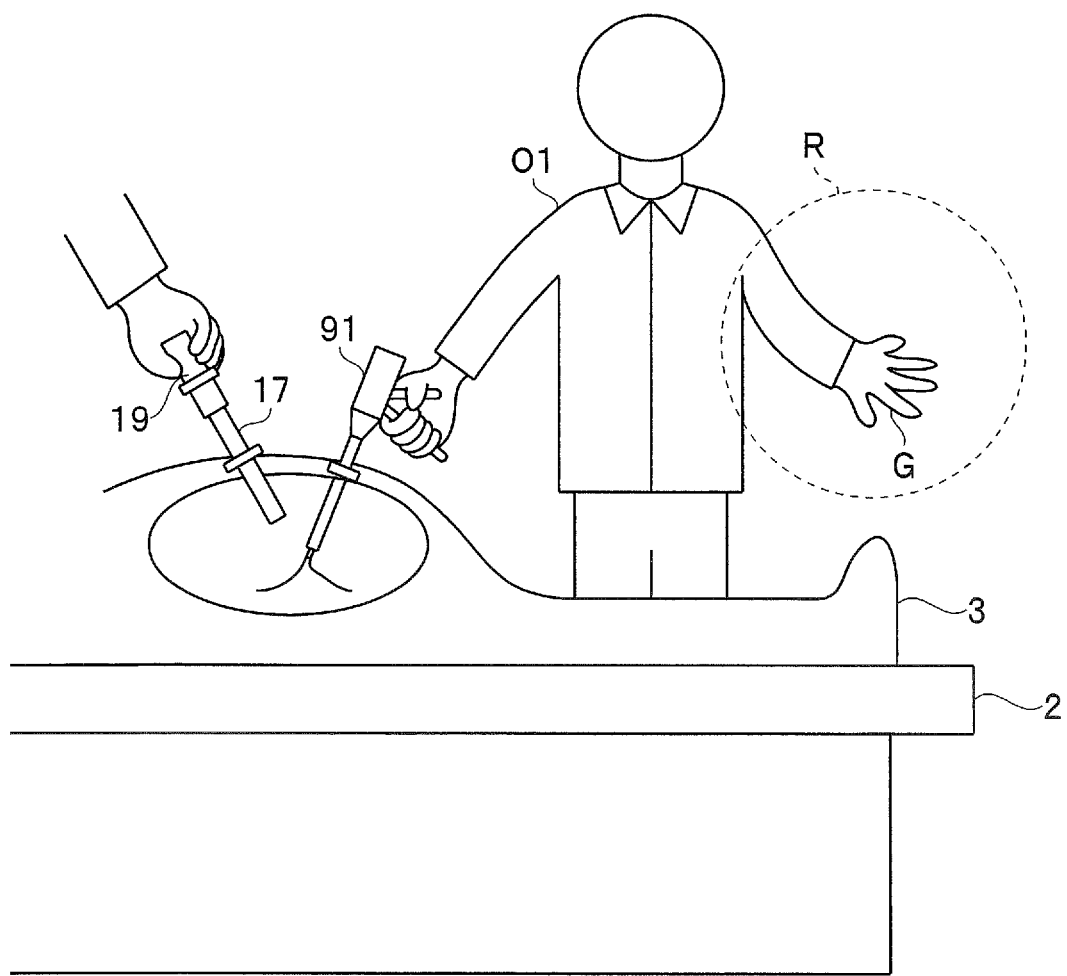
FIG. 7 is an explanatory diagram showing a state in which a surgeon performs a surgical operation and a state in which an image of a region where the surgeon performs operation of a gesture is enabled to be picked up by a camera.

On the other hand, the surgeon O1 placed in the sterilized area Dc as indicated by an alternate long and two short dashes line in FIG. 1 performs a surgical operation of the abdomen of the patient 3 using a treatment instrument. In this case, as shown in FIG. 7, the surgeon O1 operates an electric knife 91 functioning as the treatment instrument with one hand to perform treatment such as dissection of an affected part of the patient 3. When performing the treatment, the surgeon O1 performs operation of a gesture with an arm including the other hand to perform control for changing an output (high-frequency power) of the electric knife device 8 functioning as a medical instrument that supplies high-frequency power to the electric knife 91.

Note that, actually, the surgeon O1 wears a glove for surgical operation (hereinafter, simply glove) G1 on the hand that performs the operation of the gesture. The surgeon O1 performs the operation of the gesture for changing shapes of the hand wearing the glove G1 and (five fingers of) the hand in a portion of the arm, moving the arm, or the like.

To make it possible to control an operation of the medical instrument by such a gesture, the camera 62 of the terminal device 51 attached to the holder 50 is set to include, as a visual field range, a region where the surgeon O1 performs the operation of the gesture as indicated by the alternate long and two short dashes line in FIG. 1. In this case, as shown in FIG. 7, the camera 62 is set to cover, as the visual field range, a region R in which the gesture is performed in the surgeon O1 (who performs the gesture).

The camera 62 picks up an image of the region R where the operation of the gesture is performed and stores image data of the picked-up image in the image memory 72. The shape extracting section 73d has a function of a hand and arm shapes extracting section (or a hand and arm shapes extracting circuit) that extracts shapes of the hand and the arm from the image data. The recognizing section 73e recognizes, from the extracted shapes of the hand and the arm, a pattern serving as a skeleton corresponding to the shapes.

The determining section 73f determines whether the recognized pattern matches any one of a plurality of specific operation patterns by hands and arms memorized (i.e., registered) in advance in the memorizing section 74. When the recognized pattern matches any one of the operation patterns, the determining section 73f performs control to perform an operation of a medical instrument corresponding to the operation pattern.

When the terminal device 51 is attached to the holder 50, the camera 62 is fixed (stands still). Therefore, the operation of the gesture by the surgeon O1 is easily accurately recognized.

Figure 6A:
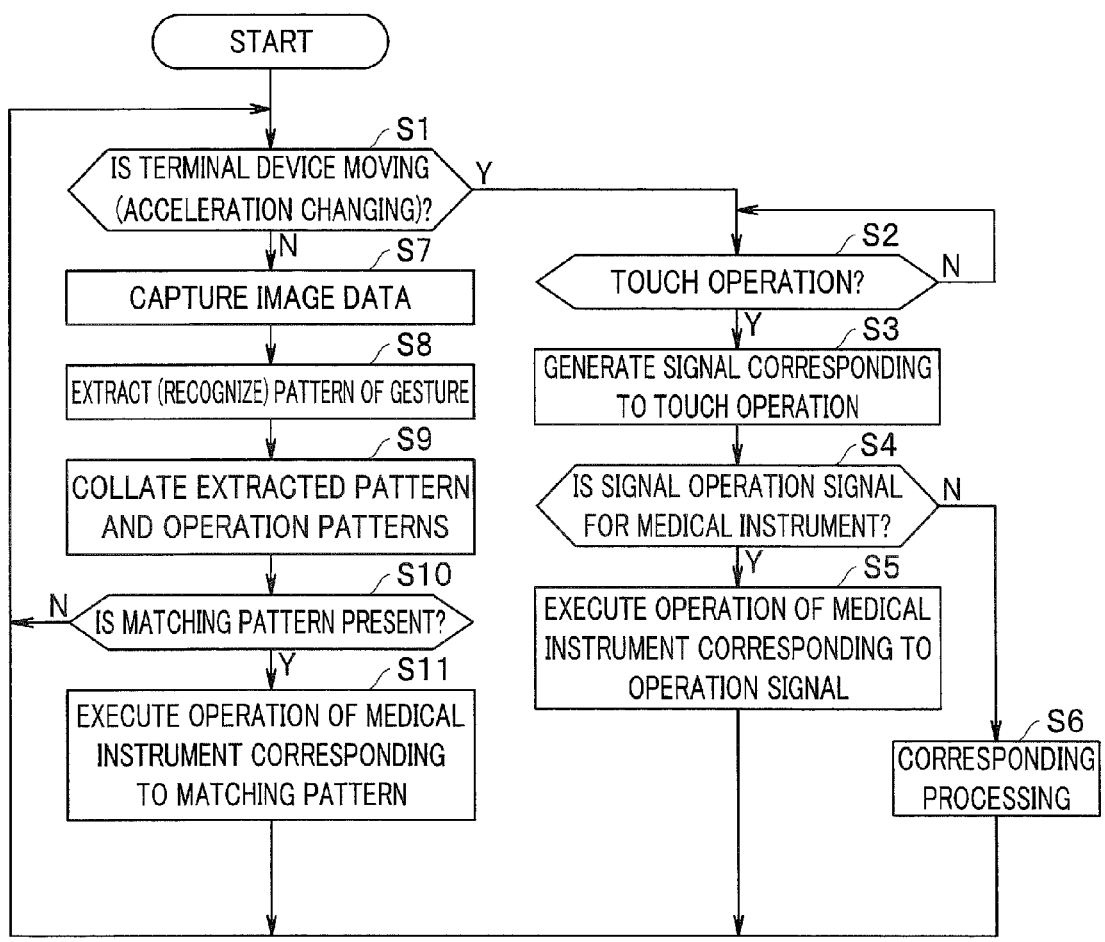
FIG. 6A is a flowchart for explaining an example of basic processing content in the first embodiment.

Basic operation in the present embodiment is similar to a processing procedure shown in FIG. 6A.

When the endoscopic surgery system 1 changes to an operating state and the terminal device 51 is also set in the operating state, in first step S1, the acceleration-change detecting section 75 in the terminal device 51 determines, from a sensing result of the acceleration sensor 75a, whether the terminal device 51 is moving (acceleration is changing). When the acceleration-change detecting section 75 determines that the terminal device 51 is moving, the switching control section 73a changes to a state in which first control by the first control section 73b is performed.

In next step S2, (the operation-position detecting section 78a of) the operation panel controller 78 determines (detects) whether the nurse N1 performs touch operation on the operation panel. When the touch operation is not performed, the operation panel controller 78 waits for the touch operation to be performed.

On the other hand, when the touch operation is performed, in next step S3, the operation-position detecting section 78b generates a signal corresponding to the touch operation and sends the signal to the first control section 73b of the CPU 73.

In next step S4, the first control section 73b determines whether the sent signal is an operation signal for causing a medical instrument to operate. When determining that the sent signal is the operation signal for causing the medical instrument to operate, in next step S5, the first control section 73b performs control to execute an operation of the medical instrument corresponding to the operation signal (or cause the medical instrument to execute the operation). The processing returns to processing in first step S1.

For example, the nurse N1 touch-operates the operation panel section 61 to set various medical instruments in setting states in actually using the medical instruments. When determining that the sent signal is the operation signal for causing the medical instrument to operate, the first control section 73b executes the operation of the medical instrument corresponding to the operation signal (or causes the medical instrument to execute the operation).

When it is determined in step S4 that the sent signal is not the operation signal for causing the medical instrument to operate, after processing (e.g., processing for wrong operation) corresponding to the signal is performed in step S6, the processing returns to the processing in step S1.

When it is not detected in step S1 that the terminal device 51 is moving, the switching control section 73a changes to a state in which second control by the second control section 73c is performed.

In this state, image pickup is performed by the camera 62 as shown in step S7. Image data generated by the driving and signal processing section 71 is sequentially captured into the image memory 72. Since the motion of the terminal device 51 is not detected in this state, the camera 62 does not move either. Therefore, in this state, a gesture of the surgeon O1 explained below is easily accurately recognized.

In next step S8, the recognizing section 73e of the CPU 73 extracts (recognizes) a pattern by a gesture of the surgeon O1 from the image data of the image memory 72. In next step S9, the determining section 73f of the CPU 73 collates the pattern extracted by the recognizing section 73e and the operation patterns of the operation pattern list of the memorizing section 74. Further, in next step S10, the determining section 73f determines whether a pattern matching the extracted pattern (a specific operation pattern) is present among the operation patterns of the operation pattern list.

When there is no pattern matching the extracted pattern, the processing returns to the processing in step S1. When the determining section 73f determines that there is a matching pattern, in next step S11, after the second control section 73c performs control to execute an operation of a medical instrument corresponding to the matching pattern (the specific operation pattern), the processing shifts to the processing in steps S1.

With the operation (the processing) shown in FIG. 6A serving as the basic operation in the present embodiment, according to a detection result of a motion of the terminal device 51, it is possible to selectively perform control of an operation of a medical instrument by touch operation of the operation panel section 61 and control of the operation of the medical instrument based on operation of a gesture by the surgeon O1 in a state suitable for the detection result of the motion.

In the present embodiment, with a processing procedure (more detailed than the processing shown in FIG. 6A) shown in FIG. 6B explained below, according to a detection result of a motion of the terminal device 51, it is possible to selectively perform control of an operation of a medical instrument by touch operation of the operation panel section 61 and control of the operation of the medical instrument based on operation of a gesture by the surgeon O1 in a state suitable for the detection result.

When the endoscopic surgery system 1 changes to the operating state and the terminal device 51 is also set in the operating state, in first step S21, the acceleration-change detecting section 75 in the terminal device 51 determines, from a sensing result of the acceleration sensor 75a, whether the terminal device 51 is moving (acceleration is changing).

Note that, in a state in step S21, the terminal device 51 is in a state in which the terminal device 51 performs radio communication with the system controller 15 (as it can be determined from step S38).

When the acceleration-change detecting section 75 determines in step S21 that the terminal device 51 is moving, the switching control section 73a changes to a state in which first control by the first control section 73b is performed. After processing in step S22 to step S26 is performed, the processing returns to the processing in step S21. The processing in step S22 to step S26 is the same as the processing in step S2 to step S6. Therefore, explanation of the processing is omitted.

On the other hand, when it is not detected in step S21 that the terminal device 51 is moving, the switching control section 73a changes to a state in which second control by the second control section 73c is performed.

In this state, as shown in step S27, the connected-state detecting section 80 detects whether the terminal device 51 is in a connected state in which the terminal device 51 is connected (attached) to the holder 50. In doing so, the connected-state detecting section 80 waits for the terminal device 51 to be changed to the connected state. When the terminal device 51 is connected (attached) to the holder 50, the electric contacts P5 and P6 change to a conducting state (as shown in FIG. 4). Therefore, a voltage at the electric contact P6 rises from a voltage at the ground G in an unconnected state to a voltage at a power supply end. The voltage increases to a threshold or more. The connected-state detecting section 80 detects a connected state (an attached state).

The connected-state detecting section 80 notifies a detection signal of the connected state to the second control section 73c. The second control section 73c receives the notification of the connected state and performs control of switching of communication, a charging operation, operation of a medical instrument by a gesture, and the like as explained below. In next step S28, the second control section 73c switches a state in which radio communication is performed to a state in which wired communication is performed. By performing the wired communication, the medical instrument is not affected by a radio wave state compared with when the radio communication is performed. Therefore, it is possible to perform more reliable communication.

In the next step S28, the charging section 82 provided in the holder 50 starts charging. A charging current flows from the charging section 82 to the battery 81 via the resistor R1. When the charging current flows, the charging-state detecting section 79 in the terminal device 51 determines whether the battery 81 is in a charging completed state in which a voltage across the resistor R1 is a threshold or less. When it is not determined that the battery 81 is in the charging completed state, charging is performed as shown in step S30.

When it is determined that the battery 81 is in the charging completed state, as shown in step S31, the charging-state detecting section 79 sends a signal for stopping the charging to the charging section 82 via the electric contacts P2 and P2'. The charging is then turned off. In step S32 after processing in steps S30 and S31, image data picked up by the camera 62 and generated by the driving and signal processing section 71 is sequentially captured into the image memory 72.

In next step S33, the shape extracting section 73d of the CPU 73 extracts a shape of a gesture of the surgeon O1 from the image data of the image memory 72. The recognizing section 73e extracts (recognizes) a pattern by the gesture from the shape extracted by the shape extracting section 73d.

In next step S34, the determining section 73f of the CPU 73 collates the pattern extracted by the recognizing section 73e and the operation patterns of the operation pattern list of the memorizing section 74. Further, in next step S35, the determining section 73f determines whether a pattern matching the extracted pattern (a specific operation pattern) is present among the operation patterns of the operation pattern list.

When there is no pattern matching the extracted pattern, the processing returns to the processing in step S29. When the determining section 73f determines that there is a matching pattern, in next step S36, the second control section 73c performs control to execute an operation of a medical instrument corresponding to the matching pattern (the specific operation pattern).

In next step S37, the second control section determines from a detection result of the connected-state detecting section 80 whether the terminal device 51 is in a state in which the terminal device 51 is connected to the holder 50. In a case of a determination result that the terminal device 51 is in the connected state, the processing returns to the processing in step S29. On the other hand, in a case of a determination result that the terminal device 51 is not in the connected state, in step S38, the second control section 73c switches the state in which the wired communication is performed to the state in which the radio communication is performed. Thereafter, the processing returns to the processing in step S21.

The surgeon O1 can instruct, without performing a gesture, the nurse N1 to, for example, increase or reduce an output setting value to the electric knife 91. However, when the surgeon O1 desires to perform treatment while slightly changing an output, it is sometimes difficult to expect that the nurse N1 changes the output appropriately as desired by the surgeon O1.

In such a case, the surgeon O1 performs a gesture for changing output setting as desired by the surgeon O1 by himself/herself, and thus the surgeon O1 can expect that the output will be changed as desired by the surgeon O1. For example, the surgeon O1 registers in advance the operation patterns and the like shown in FIG. 5 to increase an output (high-frequency power) to the electric knife 91 by a ratio proportional to a moving distance (a moving distance of a distal end) in an upward direction by performing a gesture for linearly extending an arm and a hand in a horizontal direction (a direction of 3 o'clock) and, in a state in which the arm and the hand are linearly extended, moving the distal end side in the upward direction (a direction of 2 o'clock) from the horizontal direction and to reduce the output to the electric knife 91 by a ratio proportional to a moving distance in a downward direction by performing a gesture for moving the hand at the distal end to a downward direction (a direction of 4 o'clock) from the horizontal direction. When the operation patterns and the like are registered in this way, the surgeon O1 can easily slightly change the output as desired by the surgeon O1 rather than others and perform treatment by performing operation of a simple gesture.

Note that, by limiting, according to the operation of the simple gesture, a range in which the output can be changed, in other words, limiting a range in which an output of a medical instrument is changed according to operation of a gesture, even when it is difficult to highly accurately perform pattern recognition of a gesture and collation of a recognized pattern and the operation patterns, the surgeon O1 is capable of controlling a slight output change to the medical instrument. Instead of limiting, according to the operation of the simple gesture, the range in which the output can be changed, a range in which, from an output state of a currently recognized operation pattern, the output can be changed according to an operation pattern different from the operation pattern may be limited.

When the output setting of the medical instrument is changed by a gesture, the CPU 73 may have a function of an output-change-amount limiting section 73g that limits a range in which the output is changed in this way (indicated by a dotted line in FIG. 4). When, from a first output of a medical instrument corresponding to a first pattern recognized by the recognizing section 73e, a second pattern different from the first pattern is recognized within a predetermined time period, when a second output of the medical instrument is changed according to the second pattern, the output-change-amount limiting section 73g limits a range of the output change to a threshold set in advance or less. Note that the predetermined time period is a short time period such as a time period within ten seconds. Even in this case, if a third pattern different from the second pattern and a fourth pattern different from the third pattern are prepared, it is possible to expand an output change amount. Note that, in the processing shown in FIG. 6B, the processing in step S28, step S29, and step S32 may be performed in parallel.

According to the present embodiment in which such operations are performed, the nurse N1 acting as the first operator in the non-sterilized region Dnc can control an operation of a medical instrument by, in a state in which the nurse N1 carries the terminal device 51, touch-operating the operation panel section 61 of the terminal device 51. Further, by attaching the terminal device 51 to the holder 50 in the non-sterilized area Dnc and setting the terminal device 51 in the attached state (the connected state), the operation of the medical instrument can also be controlled by the camera 62 provided in the terminal device 51 according to a gesture of the surgeon O1 in the sterilized area Dc.

Therefore, according to the present embodiment, it is possible to realize a medical portable terminal device having high convenience with which the nurse N1 in the non-sterilized area Dnc can control the operation of the medical instrument in a state suitable for a detection result of the predetermined operation state of the terminal device 51 and the surgeon O1 in the sterilized area can also control the operation of the medical instrument by performing operation of a gesture.

Note that, as explained above, in the present embodiment, when the switching control section 73a switches the control function of the first control section 73b to the control function of the second control section 73c, the function of the operation panel section 61 by the first control section 73b may be turned off. Alternatively, the control function of the first control section 73b may be turned off to limit functions that can be operated by the touch operation only to the intensive operation panel 14.

Figure 6B:
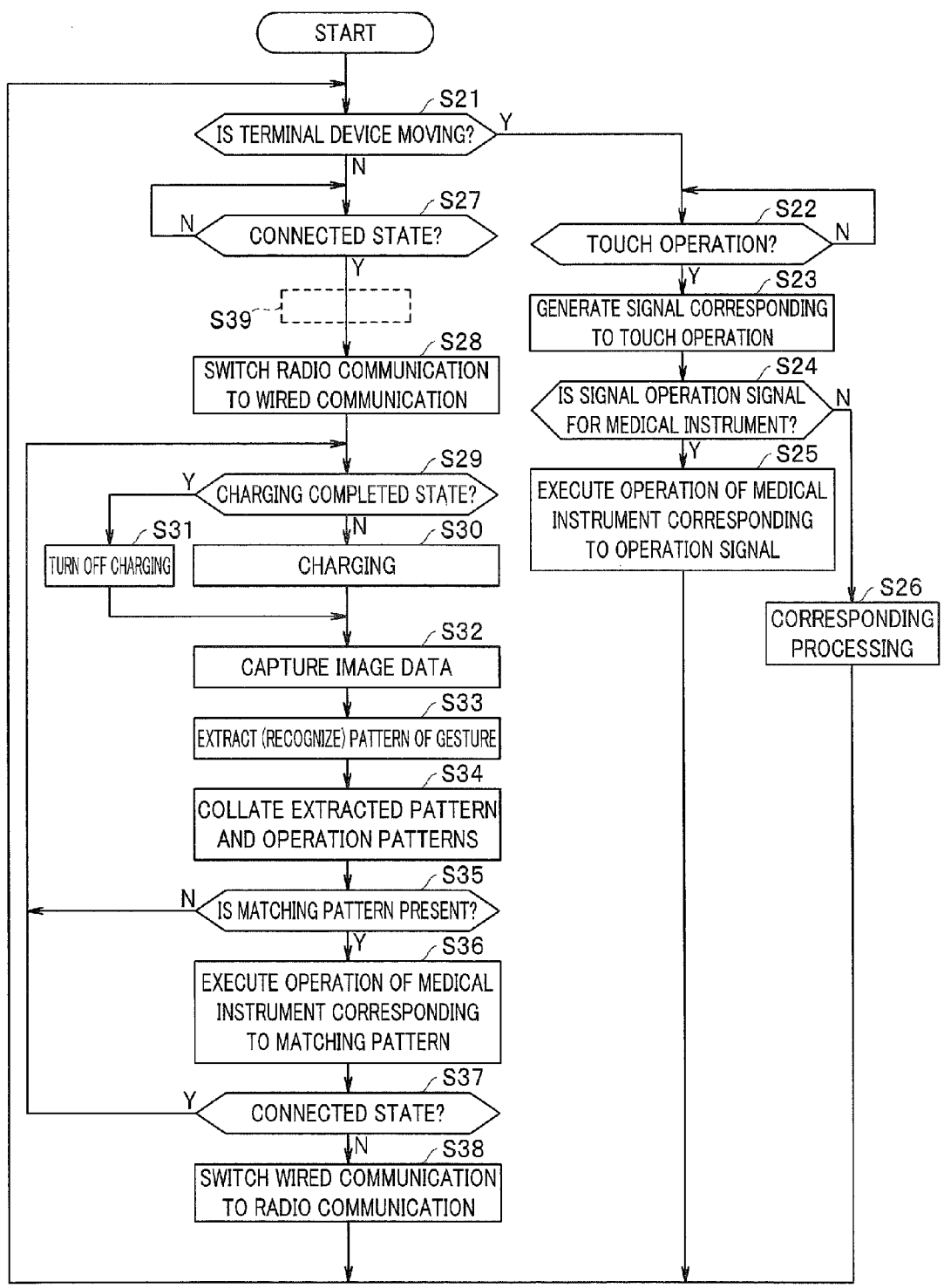
FIG. 6B is a flowchart for explaining an example of representative processing content in the first embodiment.

When such a configuration is adopted, for example, as step S39 indicated by a dotted line between steps S27 and S28 in FIG. 6B, processing for turning off the operation function of the operation panel section 61 may be included.

In an example shown in FIG. 6B, motion detection and connected state detection are performed together. However, only the motion detection may be performed as shown in FIG. 6A or only the connected state detection may be performed.

Figure 8:
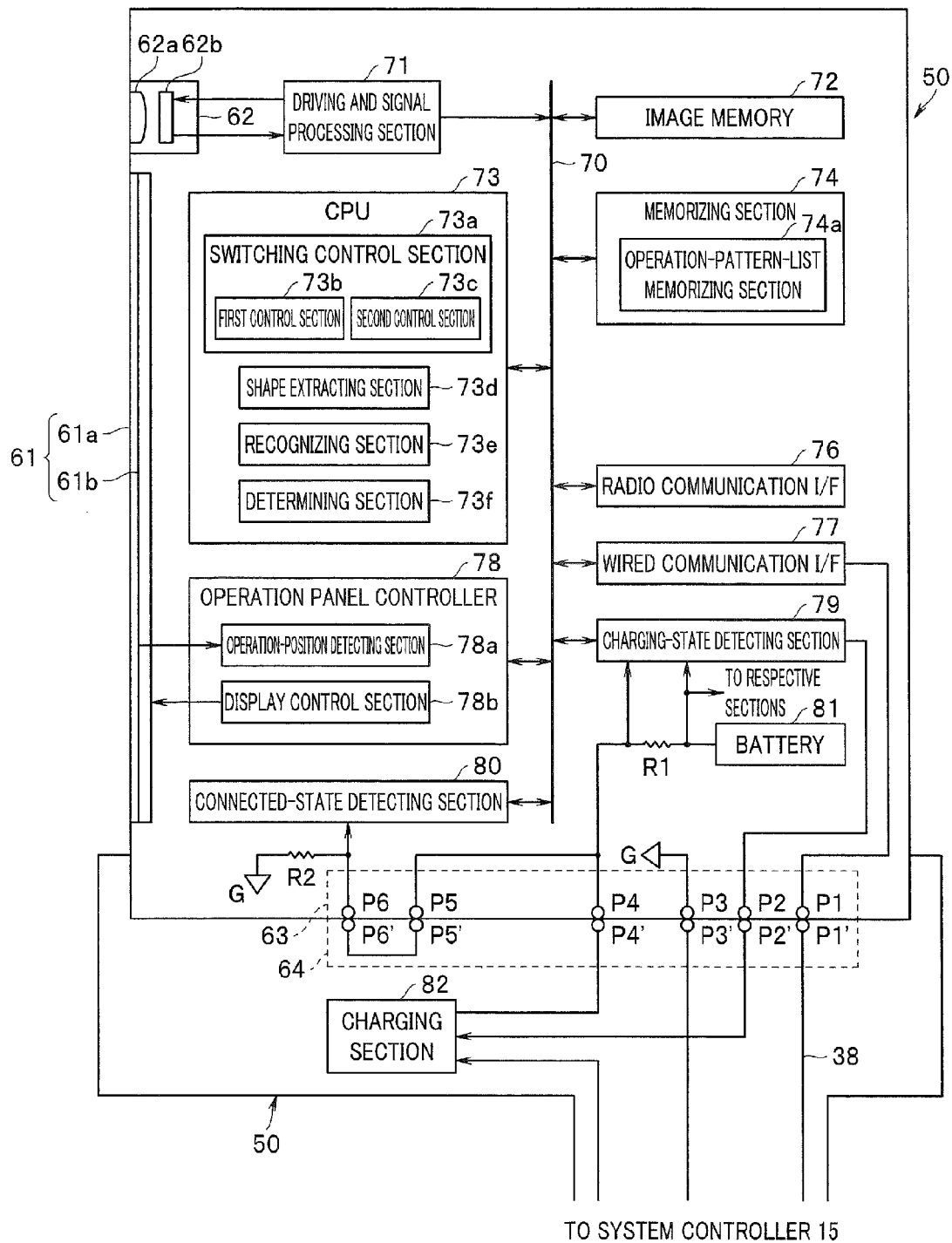
FIG. 8 is a block diagram showing a configuration of an electric system of a medical portable terminal device in a case of a first modification.

More specifically, in the configuration shown in FIG. 4 in the present embodiment, a configuration of a first modification as shown in FIG. 8 may be adopted in which the acceleration-change detecting section 75 including the acceleration sensor 75a is not provided.

Figure 9:
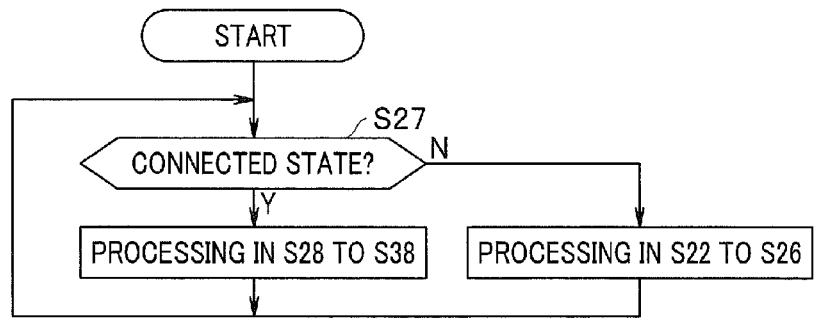
FIG. 9 is a flowchart for explaining an example of processing content in the case of the first modification.

In this case, operations as shown in FIG. 9 are performed.

In FIG. 9, processing for controlling an operation of a medical instrument by touch operation of the operation panel section 61 and processing for controlling the operation of the medical instrument on the basis of a gesture by the surgeon O1 are selectively performed according to the determination result of the connected state in step S27 without performing the processing in step S21 in FIG. 6B.

That is, in the case of the determination result that the terminal device 51 is not in the connected state in step S27, the processing in steps S22 to S26 in FIG. 6B is performed. On the other hand, in the case of the determination result that the terminal device 51 is in the connected state in step S27, the processing in steps S28 to S38 is performed.

In this case also, there are action and effects substantially the same as the action and effects in the first embodiment. Further, since the acceleration-change detecting section 75 including the acceleration sensor 75a does not have to be provided, there is an effect that it is possible to reduce costs.

A configuration in which the connected-state detecting section 80 is not provided in FIG. 8 may be further adopted to selectively perform, on the basis of detection of a charging state by the charging-state detecting section 79, the processing for controlling an operation of a medical instrument by the touch operation of the operation panel section 61 and the processing for controlling the operation of the medical instrument on the basis of a gesture of the surgeon O1.

Figure 10:
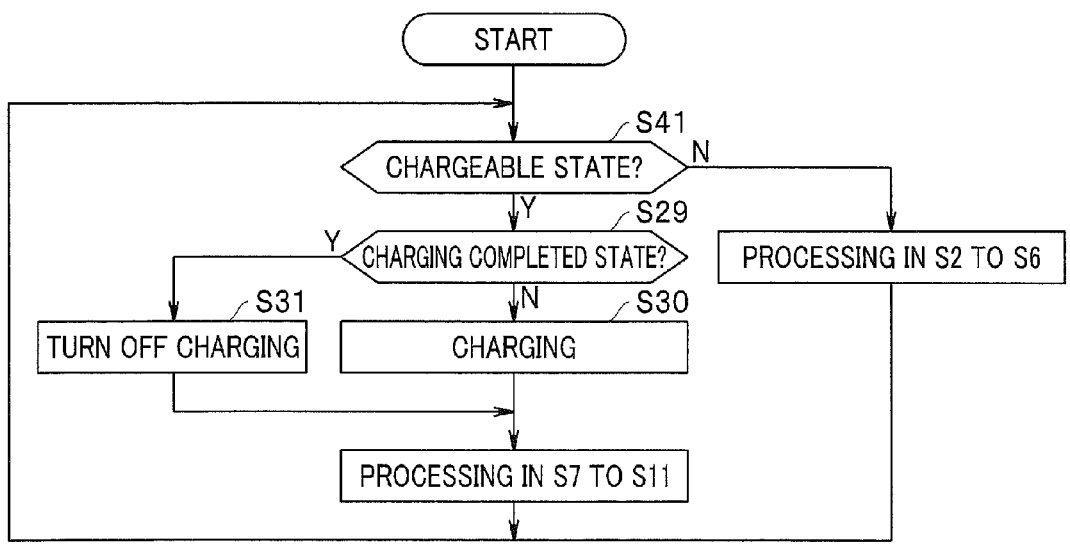
FIG. 10 is a flowchart for explaining an example of processing content in the case of a second modification.

An example of a basic processing procedure corresponding to FIG. 6A in this case is shown in FIG. 10. In first step S41, the charging-state detecting section 79 determines whether the battery 81 in the terminal device 51 is in a chargeable state.

When the terminal device 51 is connected to the holder 50, a charging current flows from the charging section 82 to the battery 81 via the resistor R1. Therefore, when the voltage across the resistor R1 is the threshold or more, the charging-state detecting section 79 determines that the battery 81 is in the chargeable state.

In a case of a determination result that the battery 81 is not in the chargeable state, the processing in steps S2 to S6 in FIG. 6A is performed. The processing returns to the processing in step S41.

In a case of a determination result that the battery 81 is in the chargeable state, the processing in steps S7 to S11 in FIG. 6A is performed. Note that, as shown in FIG. 10, in the case of the determination result that the battery 81 is in the chargeable state, further, after the processing in steps S29 to S31 explained in FIG. 6B is performed, the processing in steps S7 to S11 may be performed. That is, in the case of the determination result that the battery 81 is in the chargeable state, in step S29, the charging-state detecting section 79 further determines whether the voltage across the resistor R1 has reached a voltage equal to or lower than a voltage at which the charging to the battery 81 may be completed.

In a case of a determination result that the voltage across the resistor R has not reached the voltage in a charging completed state, a charging state is continued as shown in next step S30. On the other hand, in a case of a determination result that the voltage across the resistor R has reached the voltage in the charging completed state, the charging-state detecting section 79 sends a signal for stopping the charging to the charging section 82 as a stop signal for a predetermined period and outputs the stop signal to the charging section 82 to thereby turn off the charging (stop the charging) as shown in step S31 for a period in which the stop signal is outputted.

Note that, in a period in which the stop signal is not outputted, the charging-state detecting section 79 periodically monitors the voltage across the resistor R1 and detects whether the battery 81 is in the chargeable state and whether the voltage across the resistor R has reached the voltage in the charging completed state. After the processing in step S30 or S31, the processing in steps S7 to S11 is performed.

When the processing shown in FIG. 10 is performed, there are action and effects substantially the same as the action and effects in the first embodiment. Further, since an acceleration sensor is unnecessary, it is possible to reduce costs.

Note that the configuration shown in FIG. 4 and the like indicates one configuration example in the present invention. A configuration in which a configuration indicated by claim 1 is set as a basic configuration and one or more components are added appropriately also belongs to the present invention.

The terminal device 51 and the holder 50 functioning as the holding device that detachably holds the terminal device 51 may be defined as a medical portable terminal device or a medical portable terminal system equivalent to the medical portable terminal device.

For example, in the configuration of the terminal device 51 shown in FIG. 4 or FIG. 8, a configuration may be adopted that further includes processing and components for setting a state in which the second control section 73c can smoothly control an operation of a medical instrument according to operation of a gesture when the switching control section 73a switches the control function from the first control section 73b to the second control section 73c.

When it is determined that the terminal device 51 is moving or is in the connected state in which the terminal device 51 is connected to the holder 50, the second control section 73c changes to a state for enabling control of an operation of a medical instrument according to operation of a gesture (an operation reception state of a gesture). The second control section 73c controls an operation of a medical instrument corresponding to the operation of the gesture on the basis of a recognition result by the recognizing section 73e.

However, in some cases, the visual field range of the camera 62 configuring the image pickup section does not appropriately cover the region R where the operation of the gesture is performed by the surgeon O1. Therefore, before the second control section 73c receives the operation of the gesture, for example, the recognizing section 73e or the determining section 73f may determine whether image data of a picked-up image picked up by the camera 62 appropriately covers the region R (where the operation of the gesture is performed) and the operation of the gesture is easily recognized in a setting state.

In this case, the surgeon O1 may perform operation of a predetermined gesture corresponding to a predetermined operation pattern for determining whether the picked-up image (the visual field range) appropriately covers the region R. When recognition (determination) of the operation pattern is appropriately performed, the terminal device 51 may be set in an operation reception state of a gesture. For example, when the region R is a range of a circle, the predetermined operation pattern may be a pattern of a track drawn by a hand when operation of a gesture for drawing a circle by the hand is performed. When it can be recognized that the operation of such a gesture matches the predetermined operation pattern, the terminal device 51 may be set in the operation reception state of a gesture and thereafter perform control of an operation of a medical instrument according to the operation of the gesture as explained above.

To make it possible to perform such setting, the memorizing section 74 or the operation-pattern-list memorizing section 74a may memorize a predetermined operation pattern for determining whether the image pickup section is in a state in which the image pickup section covers the region R and appropriately picks up an image of the region R. When the operation of the gesture matches the predetermined operation pattern memorized in the memorizing section 74 or the operation-pattern-list memorizing section 74a, the recognizing section 73e or the determining section 73f may set the terminal device 51 in the operation reception state of a gesture. Consequently, when the operation of the gesture is performed, the operation of the gesture can be set in a state in which the operation of the gesture is more surely easily recognized.

Note that, in the configuration shown in FIG. 4 or FIG. 8, an operation-pattern setting section may be further provided that performs setting for, for example, adding an operation pattern to the operation-list memorizing section 74a, correcting the operation pattern, or deleting the operation pattern.

What is claimed is:

1. A medical portable terminal device for use by a first and second operator, the medical portable terminal device comprising:
 a display including a touch panel for use by the first operator that is placed in a non-sterilized area, the display being configured to control, in response to at least one touch operation on the touch panel, operations of a plurality of medical instruments disposed in the non-sterilized area;
 camera configured to record an image of a region where the second operator performs an operation of at least one gesture;
 a memory storing an operation list that causes the plurality of medical instruments to perform a plurality of operations associated with a recognized operation of the at least one gesture; and
 a processor programmed to:
  recognize the operation of the at least one gesture from the image recorded up by the camera;
  switch between control of the plurality of medical instruments based on operation of the display and control of the plurality of medical instruments based on the operation of the at least one gesture; and
  detect a predetermined operation state for the medical portable terminal device and automatically switch, on the basis of the detected predetermined operation state concerning whether the medical portable terminal device is in the predetermined operation state, between: (i) the control of the plurality of medical instruments based on the operation of the display, and (ii) the control of the plurality of medical instruments based on the operation of the at least one gesture.

2. The medical portable terminal device according to claim 1, wherein the processor is further programmed to:
 perform, when first determination is performed for the detection result concerning whether the medical portable terminal device is in the predetermined operation state, first control to cause a medical instrument corresponding to the touch operation of the display to perform an operation; and
 receive, when second determination different from the first determination is performed for the detection result concerning whether the medical portable terminal device is in the predetermined operation state, a recognition result for the operation of the gesture by the processor, compare the recognition result with the operation list stored in the memory, and perform second control for causing a medical instrument corresponding to the operation list matching the recognition result to perform an operation.

3. The medical portable terminal device according to claim 2, further comprising:

an acceleration sensor that senses acceleration acting on the medical portable terminal device and outputs a sensed signal corresponding to the sensed acceleration; wherein the processor is further programmed to:

detect, from the sensed signal, as detection concerning whether the medical portable terminal device is in the predetermined operation state, whether an absolute value of a temporal change amount of the acceleration acting on the medical portable terminal device changes by a threshold or more, perform the first control in response to the detection result that the absolute value changes by the threshold or more, and perform the second control in response to the detection result that the absolute value does not change by the threshold or more.

4. The medical portable terminal device according to claim 2, further comprising:

a connector including a plurality of electric contacts, wherein the processor is further programmed to:

detect whether the medical portable terminal device is in the predetermined operation state by detecting whether the medical portable terminal device is set in a connected state in which the connector is detachably connected to a connector receiver provided in a holding mechanism that holds the medical portable terminal device in a predetermined posture, perform the second control in response to the detection result that the medical portable terminal device is set in the connected state, and perform the first control for in response to the detection result that the medical portable terminal device is not set in the connected state.

5. The medical portable terminal device according to claim 2, further comprising:

a rechargeable battery that supplies electric power to the display, the memory, the processor, and the camera; wherein the processor is further programmed to:

detect whether the medical portable terminal device is in the predetermined operation state by detecting whether the battery is in a chargeable state, perform the second control in response to the detection result that the battery is in the chargeable state, and perform the first control in response to the detection result that the battery is not in the chargeable state.

6. The medical portable terminal device according to claim 2, further comprising:

a radio transmitter/receiver provided on an outside of the medical portable terminal device and configured to perform radio communication with a controller programmed to control the plurality of medical instruments; and at least one wired connection provided on the outside of the medical portable terminal device and configured to perform communication by wire with the controller; wherein the processor is further programmed to switch between an operation of the radio transmitter/receiver and an operation of the at least one wired connection.

7. The medical portable terminal device according to claim 2, wherein the processor is further programmed to:

limit, in performing control for changing outputs of the plurality of medical instruments on the basis of the operation of the gesture, when a state in which an output corresponding to a first pattern recognized by the processor from the operation of the at least one gesture is a first output changes to a state in which an output corresponding to a second pattern, which is different from the first pattern, recognized within a predetermined time period is a second output, a change amount from the first output to the second output within a threshold set in advance.

8. The medical portable terminal device according to claim 4, wherein the holding mechanism that holds the medical portable terminal device in the predetermined posture is configured to mechanically change a visual field range of the camera.

9. The medical portable terminal device according to claim 6, wherein the processor is further programmed to:

determine, from the image recorded by the recorded, whether the recorded image covers a region where the operation of the at least one gesture is performed.

10. The medical portable terminal device according to claim 2, wherein the memory stores a predetermined operation pattern for determining whether to cause the plurality of medical instruments to perform the plurality of operations according to the operation of the at least one gesture, and only when the processor recognizes that the second operator placed in the sterilized area separated from the non-sterilized area performs operation of a predetermined gesture corresponding to the predetermined operation pattern, the processor sets the medical portable terminal device in an operation reception state of a gesture for enabling control of the plurality of operations for the plurality of medical instruments according to the operation of the at least one gesture.

11. The medical portable terminal device according to claim 10, wherein the predetermined operation pattern is an operation pattern corresponding to an operation of at least one gesture of the second operator for drawing a track of a circle with a distal end of an arm as the operation of the predetermined gesture by the second operator.

12. The medical portable terminal device according to claim 1, wherein the camera records the image of the region where the second operator performs the operation of the gesture, the second operator being positioned in a sterilized area separated from the non-sterilized area where the plurality of medical instruments are disposed.

* * * * *